US00PP10158P

United States Patent [19]

Glaser

[11] Patent Number: Plant 10,158

[45] Date of Patent: Dec. 23, 1997

[54] AZALEA PLANT NAMED KARMA

[76] Inventor: Karl Glaser, Alte Strasse 9, D-64832 Babenhausen, Germany

[21] Appl. No.: 651,723

[22] Filed: May 22, 1996

[51] Int. Cl.[6] ..... A01H 5/00

[52] U.S. Cl. ..... Plt./56

[58] Field of Search ..... Plt./56

*Primary Examiner*—James R. Feyrer
*Assistant Examiner*—Melissa L. Kimball

[57] ABSTRACT

An azalea plant named Karma particularly characterized by its evergreen foliage, semi-double flowers, dark pink flower color, free branching, compact semi-upright plant habit, uniform flowering response in a year round controlled program, and by its good cooler tolerance and keeping quality.

1 Drawing Sheet

The present invention comprises a new and distinct cultivar of Azalea, a greenhouse forcing type hereinafter referred to as Karma.

Karma, identified as 2–3 during the selection process, originated from a planned cross hybridization between two selected breeding lines in a controlled breeding program in Babenhausen, Germany by the inventor Karl Glaser.

The female, or seed parent of Karma is an unnamed seedling having large pink single shaped flowers, a round habit, and dark green foliage. The male, or pollen parent is an unnamed seedling, with red funnel-shaped flowers, a round habit, and green foliage.

Karma was discovered and selected as one flowering plant within the progeny of the stated cross by the inventor Karl Glaser in January 1982 in Babenhausen, Germany.

The first asexual reproduction of Karma was accomplished when vegetative cuttings were taken from the initial selection in April 1982, in Babenhausen, Germany, by technicians working under formulations established and supervised by Karl Glaser.

Horticultural examination of controlled flowerings of successive generations of plants derived from cuttings taken from the original selection has shown that the unique combination of characteristics as herein disclosed for Karma are fixed and retained through successive generations of asexual reproduction.

Karma has not been observed under all possible environmental conditions. The phenotype may vary significantly with variations in environment such as temperature, light intensity and day length, without, however, any variance in the genotype.

The following observations, measurements and comparisons describe plants that were grown in Salinas, Calif. in a controlled greenhouse environment and following a commercial schedule.

The following traits have been repeatedly observed and are determined to be basic characteristics of Karma, which in combination distinguish this azalea as a new and distinct cultivar:

1. A dark-pink flower color (between 57D and 58C) upon opening, fading to a lighter pink (67D) as flowers age.
2. Semi-double flowers, with the flowers ranging from 7.0 to 10.0cm in diameter, with 8.5cm the average size.
3. Compact, semi-upright, free branching plant habit.
4. Uniform response in year round controlled flowering programs, forcing in 20 days on average.
5. Long lasting flowers, with flowers in a simulated home environment lasting up to two weeks.
6. Medium green pubescent evergreen foliage, leathery in appearance.
7. Good foliage retention and no flower bud damage when cooled for 6 weeks with no lighting at 38° F.

The accompanying color photograph shows in perspective view the unique features of the new cultivar, with colors being as true as possible with color illustrations of this type.

Of the commercial cultivars known to the inventor, the most similar in comparison to Karma is the cultivar Solitaire, disclosed in U.S. Plant Pat. No. 3,171. General flower color (pink category) and flower response are similar. Karma differs from Solitaire in that the flowering Karma are larger and darker pink in color. The foliage of Karma also is darker green and larger than that of Solitaire.

In the following description color references are made to The Royal Horticultural Society Color Chart. The color values were determined on Apr. 20, 1995. All readings were taken in an office under cool white fluorescent lights, facing a west window between the hours of 10:00 a.m. and 2:00 p.m.

Classification:

*Botanical.*—Rhododendron hybrida evergreen type, c.v. 'Karma'.

*Commercial.*—Florist forcing pot azalea.

INFLORESCENCE

A. Flowers (General):

*Size.*—7.0 to 10.0 cm.

*Borne.*—Terminal cluster, usually 2 per bud, ranging from 1–3. Often more than one bud per stem.

*Form.*—Semi-double funnel-form.

*Blooming habit.*—Once, profusely. Buds easily and uniformly in a year round program. The majority of terminal buds break color within one week of the first. Flowering begins approximately 20 days after the start of forcing.

*Fragrance.*—None.

B. Corolla (Petals):

*Texture.*—Soft.

*Substance.*—Heavy.

*Shape.*—Rounded.

*Color (fully open).*—Generally between 57D and 58C, fading to 67D as flowers age. Upper surface: Edge: Between 57D and 58C. Center: Between 57D and 58C. Base: 58D. Lower surface: 61D. Blotch: 61C.

C. Bud:

*Size.*—Medium.

*Shape.*—Conoidal.

*Color.*—66C.

*Bud sheath.*—Immature: Light green with light brown hairs. Mature: Brown with light brown hairs.

D. Calyx:

*Form.*—Rounded.

*Color.*—144A.

E. Peduncle:

*Length.*—0.5 to 1.6 cm.

*Strength.*—Strong.

*Aspect.*—Pubescent.

F. Reproductive organs:

*Androecium (stamens).*—Number: 0 to 5. Many are fully or partially petaloid. Anthers: Pink. Filaments: Length: 0.0 to 1.9 cm. Color: Dark pink.

*Gynoecium (pistil).*—Stigma: 91A. Style: Length: 1.6 to 3.8 cm. Color: 91C. Ovary: Pubescent.

PLANT CHARACTERISTICS

A. Foliage:

*Type.*—Evergreen.

*Arrangement.*—Alternate.

*Shape.*—Elliptic.

*Size.*—Length: 2.0 to 7.2 cm. Width: 1.0 to 3.5 cm.

*Margin.*—Entire.

*Color.*—Immature: Upper Surface: Between 143C and 144A. Lower Surface: 146C. Mature: Upper Surface: 147A. Lower Surface: 147B. Texture: Leathery. Tomentum: Present on upper surface. Insignificant.

B. Stems:

*Color.*—Immature: 144A. Mature: 165A. Tomentum: Present, but insignificant.

C. Plant habit: Compact, semi-upright bush which achieves a uniform, symmetrical plant in a six inch pot when pinched three times. Total crop time to the dormant budded stage is 40–42 weeks to produce a plant 26–34cm in diameter and 24–33cm in total height. Internode lengths vary from 2–17mm.

D. Branching habit: Free branching, producing 3–4 breaks when a vegetative cutting is pinched.

E. Rooting: Roots easily in 8 to 10 weeks with 75° F. soil temperature.

F. Budding ease: Plants produce flower buds easily and uniformly year round with the use of commercially available plant growth regulators. Karma has a medium natural season response time.

Cooler tolerance: Plants placed in a cooler as a means of breaking dormancy perform well. Karma is tolerant of six weeks in an unlighted cooler at 38° F. without foliage loss or bud damage.

H. Blooming: Plants reach the stage of 12 buds showing color in 20 days on average after the cooler treatment. This varies from 13 to 30 days depending upon temperature and stage of flower bud development at the start of forcing. Karma flowers uniformly and profusely across the plant and down the sides.

I. Shelf life: When plants are moved to an office environment at the stage of eight open flowers they maintain an attractive appearance for up to two weeks. Flowers are somewhat persistent, only occasionally dropping as flowers become old.

I claim:

1. A new and distinct cultivar of azalea plant named Karma as described and illustrated.

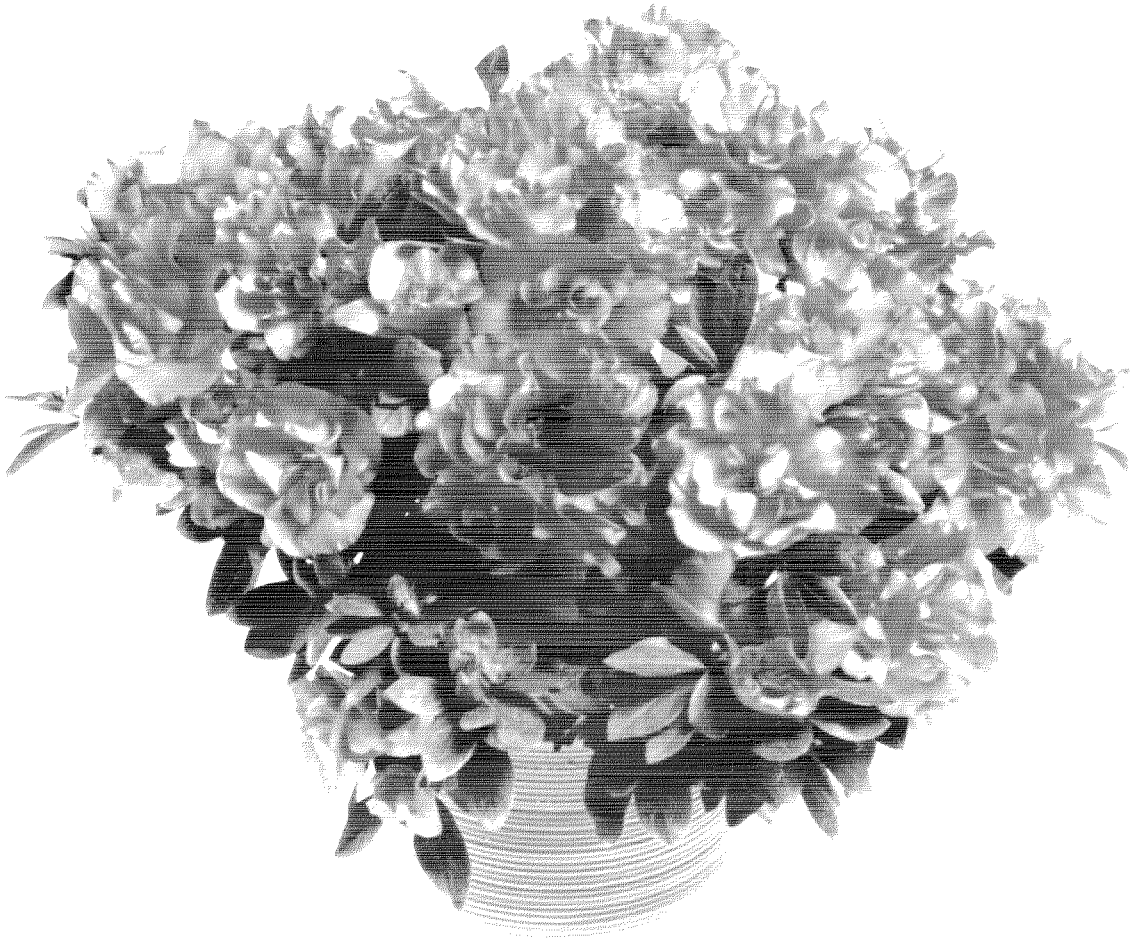

* * * * *